US008372111B2

(12) United States Patent
Reyna

(10) Patent No.: US 8,372,111 B2
(45) Date of Patent: Feb. 12, 2013

(54) SYSTEM AND METHOD FOR APPLYING PRESSURE TO HUMAN TISSUE

(76) Inventor: Victor R. Reyna, Houston, TX (US)

( * ) Notice: Subject to any disclaimer, the term of this patent is extended or adjusted under 35 U.S.C. 154(b) by 799 days.

(21) Appl. No.: 12/432,915

(22) Filed: Apr. 30, 2009

(65) Prior Publication Data

US 2010/0280542 A1 Nov. 4, 2010

(51) Int. Cl.
*A61B 17/00* (2006.01)

(52) U.S. Cl. ............ 606/204; 606/201; 601/51; 601/53; 601/68; 601/84; 601/94; 601/129; 601/135; 601/137

(58) Field of Classification Search .................. 606/204; 601/51, 53, 68, 84, 94, 129, 134–137
See application file for complete search history.

(56) References Cited

U.S. PATENT DOCUMENTS

| | | | | | |
|---|---|---|---|---|---|
| D377,100 | S | * | 12/1996 | Gladieux, Jr. | D24/211 |
| D408,924 | S | * | 4/1999 | Chen | D24/211 |
| 6,241,694 | B1 | * | 6/2001 | Goulding-Thompson et al. | 601/135 |
| 6,251,089 | B1 | * | 6/2001 | Kuznets et al. | 601/95 |
| 6,726,640 | B2 | * | 4/2004 | Ching-Chen | 601/125 |
| 2002/0151930 | A1 | * | 10/2002 | Mills | 606/204 |
| 2004/0006293 | A1 | * | 1/2004 | Huang | 601/134 |

* cited by examiner

*Primary Examiner* — Gary Jackson
*Assistant Examiner* — Kevin Everage
(74) *Attorney, Agent, or Firm* — G Michael Roeback, PC

(57) ABSTRACT

An apparatus is disclosed including but not limited to a group of force resistive objects for concurrently applying pressure to different positions on at least one of a plurality of human tissues; and a connective member for fixedly interconnecting the plurality of force resistive objects. A method for using the apparatus is also disclosed.

10 Claims, 6 Drawing Sheets

Top View

Side View

SYSTEM AND METHOD FOR APPLYING PRESSURE TO HUMAN TISSUE

BACKGROUND

1. Field of the Invention

The present invention relates to the field of physical manipulation of human tissue.

2. Related Art

Technically speaking, sciatica is a symptom not a diagnosis. It is a non-specific term commonly used to describe symptoms of pain radiating downward from the buttock over the posterior or lateral side of the lower limb. It is usually assumed to be caused by compression of a nerve but this is not necessarily so. A common neurological cause of this pain is entrapment of the sciatic and/or posterior femoral cutaneous nerves. But the pain may be caused by trigger points in the soft tissue.

SUMMARY OF THE INVENTION

Figure 1A:
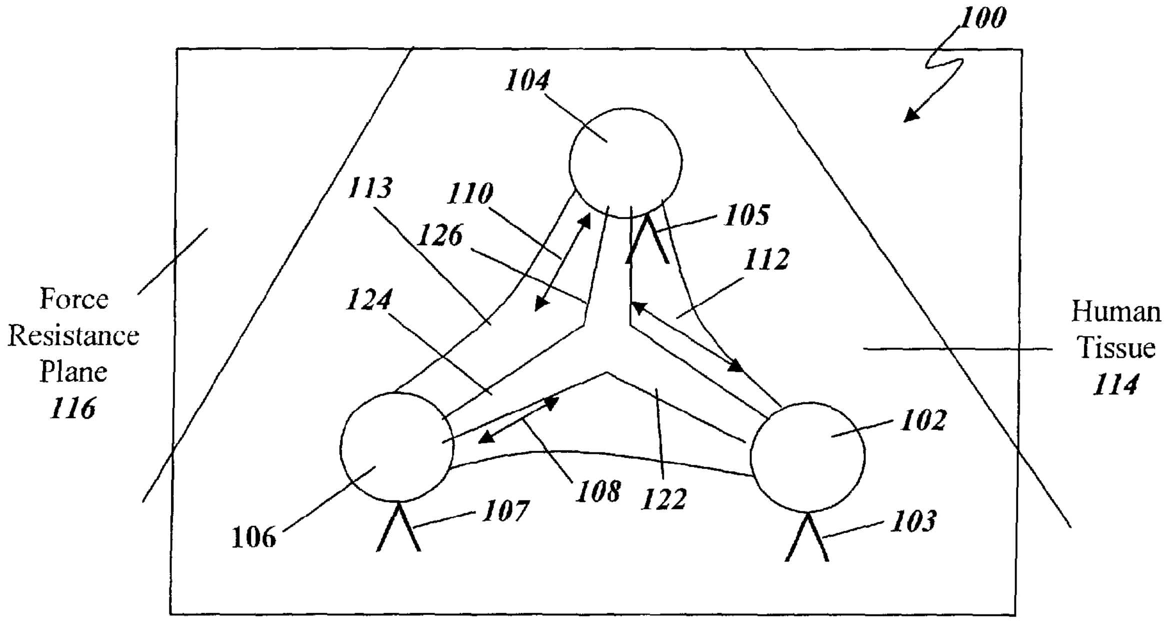
FIG. 1A depicts a top view of an illustrative embodiment of the present invention.

An apparatus is disclosed including but not limited to a group of force resistive objects for concurrently applying pressure to different positions on at least one of a plurality of human tissues; and a connective member for fixedly interconnecting the plurality of force resistive objects. A method for using the apparatus is also disclosed.

DETAILED DESCRIPTION

As the sciatic nerve passes through the buttock it goes through or under a muscle called the 'Piriformis'. This muscle lies deep to the large buttock muscles (Gluteus maximus and medius) and is classified as a lateral (outward) rotator of the hip when it is in a neutral weight-bearing position as in standing or when extended during walking or running. In addition, it abducts (away from the center) the thigh when flexed. It also plays a restraining role by controlling medial rotation (inward) during the initial stance phase of walking or running. Sustained tension in this muscle can lead to the formation of trigger points resulting in the compression of the sciatic nerve and possibly the dysfunction of the SI joint (joint between the spine and the pelvis).

Trigger points in the piriformis are very common, and are usually involved to some extent anytime there is pain in and coming from the gluteal/pelvic region. It is commonly called "piriformis syndrome." Females are affected far more than males, with a ratio of 6:1. When the piriformis muscle is enlarged, it easily entraps the sciatic nerve and other major nerves and blood vessels. Even if there is entrapment, there are also likely trigger points, which may be part of the cause of the entrapment, since trigger points may cause the muscle to bulge.

An illustrative embodiment applies pressure to one or more of these trigger points and has been found to relieve pain. In another illustrative embodiment, a particular illustrative embodiment of an apparatus is disclosed, including but not limited to a plurality of force resistive objects for concurrently applying pressure to a plurality of different positions on at least one of a plurality of human tissues; and a connective member for fixedly interconnecting the plurality of force resistive objects. In another particular embodiment of the apparatus, the force resistive objects concurrently apply pressure to the human tissues at the plurality of different positions and are fixedly interconnected in a geometric configuration selected from the group consisting of a triangle, rectangle, square, parallelogram and irregular. In another particular embodiment of the apparatus, the objects have a shaped selected from the group consisting of a pyramid, sphere, square, cylinder and oval. In another particular embodiment of the apparatus, the connective member is adjustable to change a distance between at least two of the interconnected objects and at least one of the different positions. In another particular embodiment of the apparatus, the plurality of objects further comprise a material having a property selected from the group consisting of piezoelectric, elastomeric, electro transmissive, heat absorptive, heat generating and cold generating. In another particular embodiment of the apparatus, the objects further comprise an inner portion comprising an inner material surrounded by an outer portion comprising a flexible material, wherein the inner material is selected from the group consisting of a gel, a liquid, a powder and a solid. In another particular embodiment of the apparatus, the connective member is elastic so that a variable force is reduced on the object and the reduced force allows the elastic connective member when stretched to contract and change position to move the object to different positions on the human tissues.

In another particular embodiment of the apparatus, the human tissues further comprises tissue selected from the group consisting of bone, muscle and nerve, wherein each of the plurality objects resists force from at least one of the human tissues. In another particular embodiment of the apparatus, at least two of the objects resist force from at least two different tissues at separate positions on the human body. In another particular embodiment of the apparatus, at least three of the objects resist force from at three different tissues at separate positions on the human body. In another particular embodiment of the apparatus, the connective member is elastomeric the apparatus further includes but is not limited to an electronic controller for stimulating the elastomeric connective member to contract and expand the elastomeric connective member to change the position of the objects.

In another particular embodiment, a method is disclosed, the method including but not limited to concurrently applying a force from human tissues to a plurality of interconnected force resistive objects, at a plurality of different positions on the human tissues. In another particular embodiment of the method, applying the force concurrently applies a pressure to the human tissue at the plurality of different positions the objects are fixedly interconnected in a geometric configuration selected from the group consisting of a triangle, rectangle, square, parallelogram and irregular. In another particular embodiment of the method, the objects have a shape selected from the group consisting of a pyramid, sphere, square, cylinder and oval. In another particular embodiment of the method, the method further includes but is not limited to adjusting a length of the connective member to change a distance between at least two of the interconnected objects to change at least one of the plurality of different positions on the human tissues.

In another particular embodiment of the method, the objects further comprise an object material having an object property selected from the group consisting of piezoelectric, elastomeric, electro transmissive, heat absorptive, heat generating and cold, the method further including but not limited to stimulating the object material to manifest the object property; and transferring an effect manifested by the object property to at least one of the human tissues to at least one of the plurality of positions on the human tissues. In another particular embodiment of the method, each of the plurality of objects further comprise a center portion comprising a inner material surrounded by a outer portion comprising a outer material, wherein the inner material is selected from the group consisting of a gel, a liquid, a powder and a solid and the outer material is flexible, the method further including but not limited to changing a force applied to one of the plurality of the human tissues to at least one of the positions by exchanging a first one of the plurality of objects comprising a first combination of inner and outer materials with a second one of the plurality of objects comprising a second combination of inner and outer materials.

In another particular embodiment of the method, the connective member is elastic, the method further including but not limited to stretching the connective member; and applying a reduced force on at least one of the objects allowing the stretched connective member to contract and move the object from a first position on the human tissue to a second position on the human tissue. In another particular embodiment of the method, the human tissues further comprises tissue selected from the group consisting of bone, muscle and nerve, wherein each object resists force from at least one of the human tissues, the method further comprising: placing the apparatus on a seat of a chair and sitting on the apparatus to apply pressure to the human tissues at different positions on the human body. In another particular embodiment of the method, the method further includes but is not limited to applying resist force from at two different tissues at separate positions on the human body from at least two of the objects. In another particular embodiment of the method, the method further includes but is not limited to applying resistive force from at three different tissues at separate positions on the human body from at least three of the objects. In another particular embodiment of the method, the connective member is elastomeric the method further including but not limited to applying an electronic stimulus from an electronic controller for stimulating the elastomeric connective member to contract and expand the elastomeric connective member to change the position of the objects.

Turning now to FIG. 1A, a top view 100 of an illustrative embodiment is depicted. As shown in FIG. 1A, a particular illustrative embodiment includes but is not limited to an apparatus which includes but is not limited to a plurality of interconnected force resistive objects 102, 104 and 106 interconnected by connective members 122, 124 and 126. In another particular embodiment, connective members 122, 124 and 126 expand and contract along lines 112, 108 and 110 to change the positions 103, 107 and 105 of force resistive objects 102, 106 and 104 respectively. In a particular illustrative embodiment a skin 113 covers the entirety of the connective members and force resistive members. As shown in FIG. 1A, the force resistive objects are placed on top of a force resistive plane. The force resistive plane can include but is not limited to a chair, an automobile seat or the floor. In a particular embodiment, a human sits on top the force resistive objects. The force resistive objects contacting the force resistive plane, act to oppose or resist the force of the weight of the human sitting one the force resistive objects.

The force resistive objects apply pressure to the human tissues at the points or regions on the human tissue which are coincident with the positions 103, 105 and 107 of the force resistive objects. Thus, pressure can be applied concurrently to the human tissues at the points or regions on the human tissue which are coincident with the positions 103, 105 and 107 of the force resistive objects. The position of points or regions on the human tissue which are coincident with the positions 103, 105 and 107 of the force resistive objects can be changed by moving the human sitting on the force resistive objects or by changing the position of the force resistive objects by adjusting the connective member to change the positions of the force resistive objects relative to one another.

Each of the force resistive objects can be positioned to apply pressure to different tissues concurrently. Thus, the force resistive objects can be positioned to apply pressure to multiple tissues at the same time. The force resistive objects to human tissues, including but not limited to muscle, bone and nerves are placed on top of the force resistive objects. A is force applied to the force resistive objects from the human tissue. The force resistive objects can also be positioned to apply pressure to multiple points on the same tissue. As discussed below in connection with FIG. 8, in one particular embodiment, the force resistive objects can be positioned to apply pressure to two piriformis muscle trigger points and the sciatic nerve concurrently.

Figure 1B:
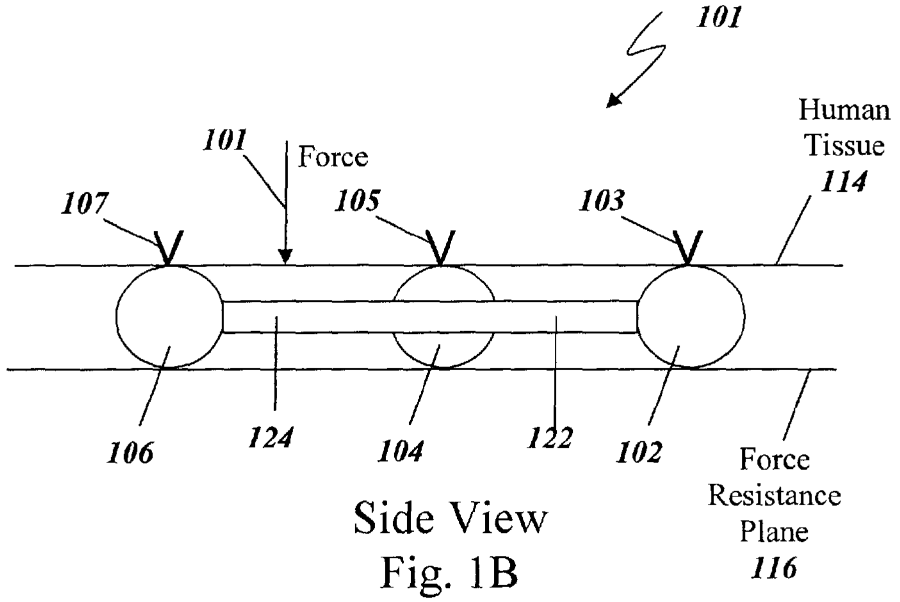
FIG. 1B depicts a side view of the illustrative embodiment shown in FIG. 1A.

Turning now to FIG. 1B, a side view 101 of the illustrative embodiment depicted in FIG. 1A. As shown in FIG. 1B, the force resistive objects contact force resistive plane 116. The force generated 101 of the human's weight sitting on top of the pressure resistive objects applies pressure to the human tissue 114 at points 103, 105 and 107 coincident with pressure resistive objects 102, 104 and 106.

Figures 2A, 2B, 2C, 2D, 2E, 2F:
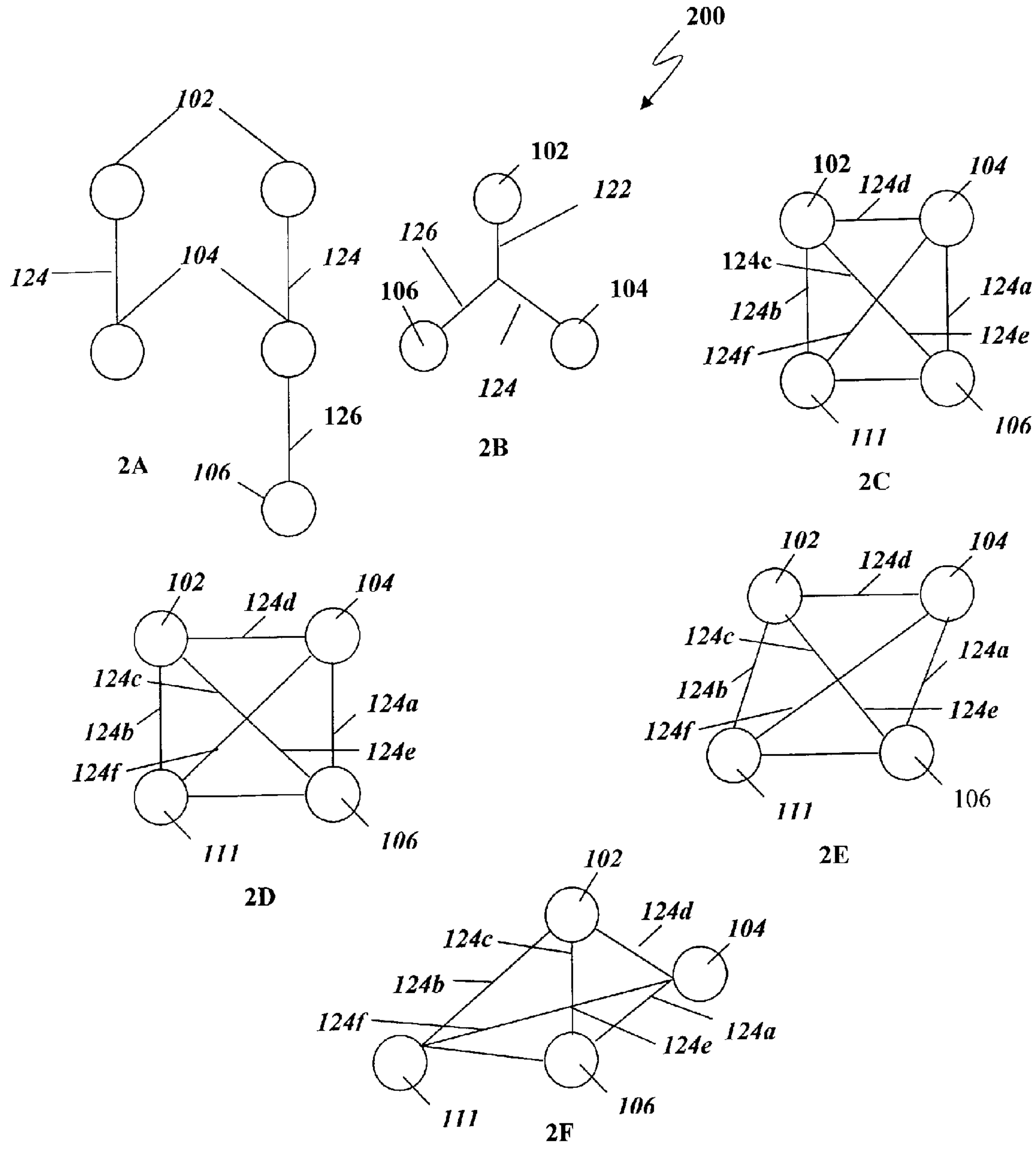
FIGS. 2A-2E depict various different illustrative embodiments having different geometric configurations of force resistive objects.

Turning now to FIGS. 2A-2F, in another illustrative embodiment there can be only two objects. In another illustrative embodiment, there can be four or more interconnected objects. As shown in FIG. 2A, in one particular embodiment, force resistive objects 102 and 104 can be connected together by connective member 124 to form an apparatus with two force resistive objects forming a straight line and force resistive objects 102, 104 and 106 are connected together with connective members 124 and 126 to form a straight line. As shown in FIG. 2B, force resistive objects 102, 104 and 106 are connected together with connective members 124 and 126 to form a triad or triangular shaped geometric pattern. As shown in FIG. 2C, force resistive objects 102, 104, 106 and 111 are connected together with connective members 124_a_-124_f_ to form a square geometric pattern. As shown in FIG. 2D, force resistive objects 102, 104, 106 and 111 are connected together with connective members 124_a_-124_f_ to form a square geometric pattern. As shown in FIG. 2E, force resistive objects 102, 104, 106 and 111 are connected together with connective members 124_a_-124_f_ to form a parallelogram geometric pattern. As shown in FIG. 2F, force resistive objects 102, 104,

106 and 111 are connected together with connective members 124*a*-124*f* to form an irregular geometric pattern.

Figure 3:
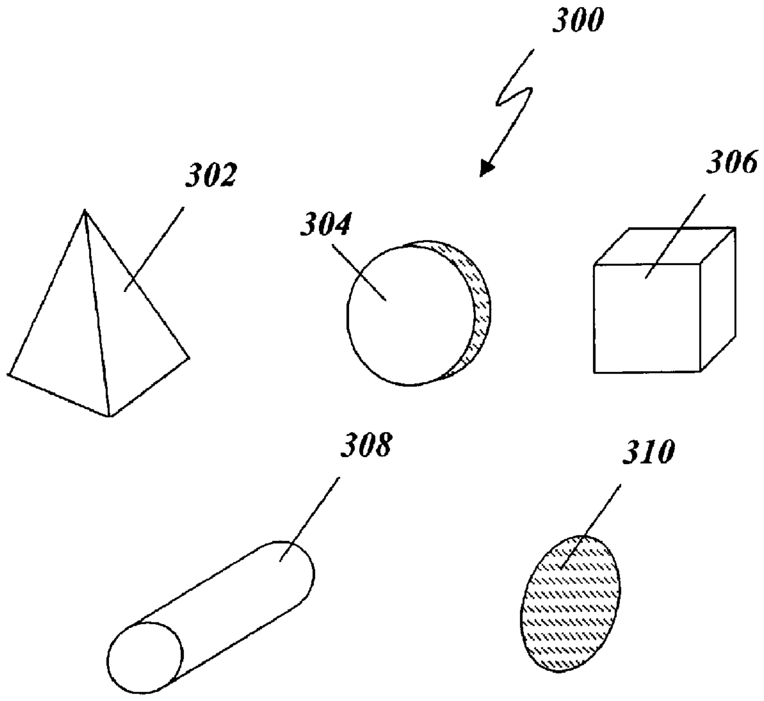
FIG. 3 depicts various different illustrative embodiments having different geometric shapes for the force resistive objects.

Turning now to FIG. 3, the force resistive objects 102, 104, 106 and 111 are made in at least one of many three dimensional geometric shapes, including but not limited to a cube, ellipsoid, pyramid, cylinder, and an irregular shape as shown in FIG. 3. Different shapes can be selected to change the focus of physical impact which the force resistive object delivers to the human tissues applying a pressure thereto.

Figure 4:
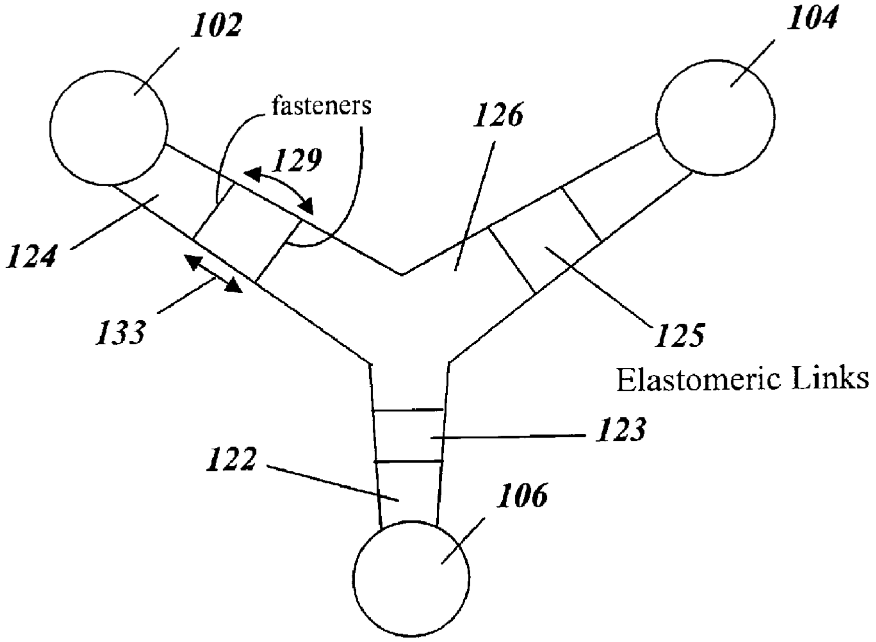
FIG. 4 depicts another particular illustrative embodiment of the present invention having adjustable positions.

Turning now to FIG. 4, in another particular illustrative embodiment, a mechanical fasteners 129 such as a zippers, hooks, Velcro pieces or plastic tongue in grove connectors are provided to shorten a connective member, such as connective member 124 to reduce the connective member length by distance 133 caused by connection of mechanical fasteners 129. Also as shown in FIG. 4, elastomeric members 123 and 125 can be inserted into connective members 122 and 126 respectively to replace all or a portion of a connective member. The elastomeric member is manipulated electronically by stimulator 402 (shown below on FIG. 5A and FIG. 5B) to expand and contract to change the lengths of elastomeric members 123 and 125 thereby changes the lengths of connective members 122 and 126 and the positions of force resistive members 104 and 106 respectively.

Figure 5A:
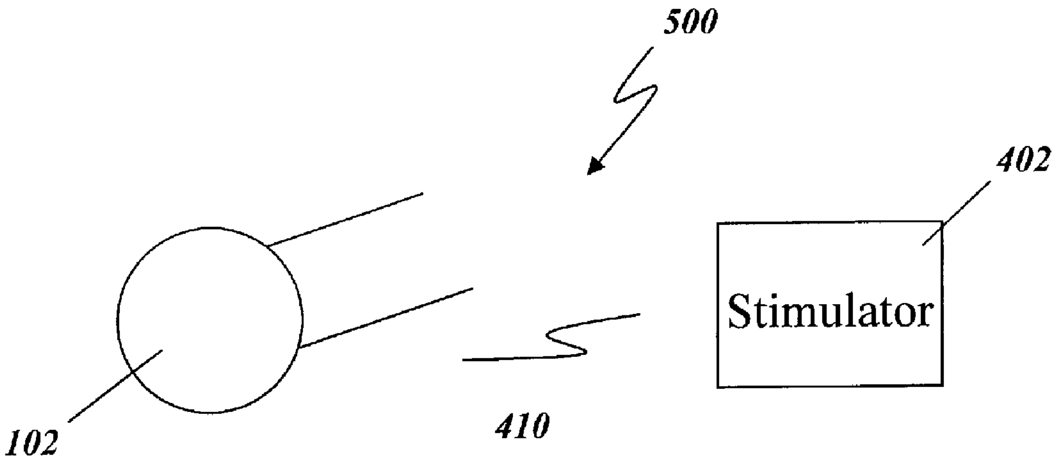
FIG. 5A depicts another illustrative embodiment having a wireless external stimulator.
Figure 5B:
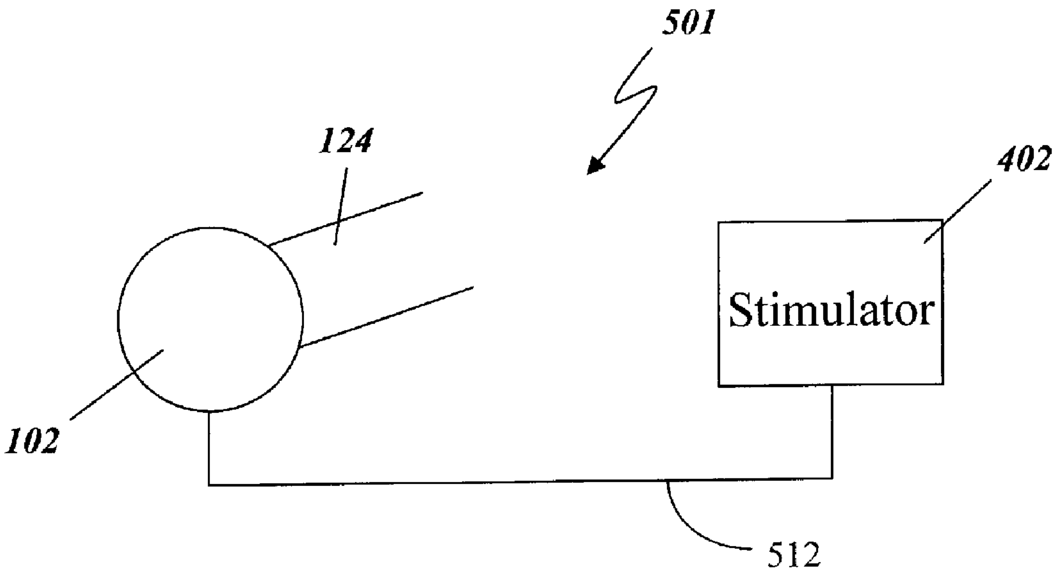
FIG. 5B depicts another illustrative embodiment having a wired external stimulator.

Turning now to FIGS. 5A and 5B, stimulator 402 applies a stimulus to force resistive object 102. The force resistive object can be made of various materials which exhibit specific properties when the stimulus 410 is applied by stimulator 402. In a particular embodiment, the force resistive object 102 is made of a piezoelectric material and stimulator 402 is an electronic circuit for applying electrical energy (wireless FIG. 5A or direct wired as in FIG. 5B) the piezoelectric material in force resistive object 102 to cause the piezoelectric material to vibrate. In another particular embodiment, the force resistive object 102 is made of an elastomeric material and stimulator 402 is an electronic circuit for applying electrical energy (wireless or direct wired) the elastomeric material in force resistive object 102 to cause the elastomeric material to expand and contract to massage human tissue in which it comes in physical contact. In a particular embodiment, the force resistive object 102 is made of a heat generating material and stimulator 402 is an electronic circuit for applying electrical energy (wireless or direct wired) the heat generating material in force resistive object 102 to cause the heat generating material to apply heat to human tissue in which it comes in physical contact.

Figure 6:
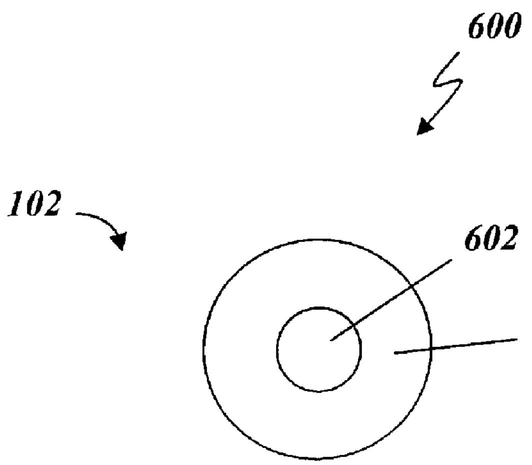
FIG. 6 depicts another illustrative embodiment having an inner and outer portion.
Figure 7:
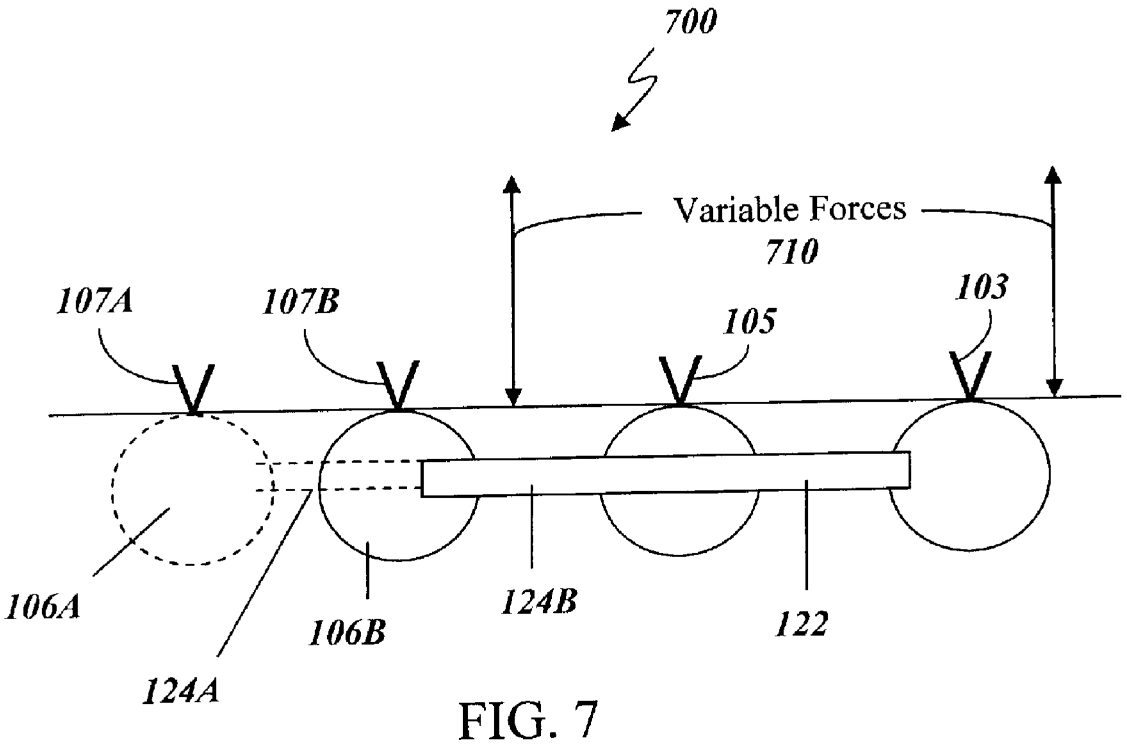
FIG. 7 depicts an illustrative embodiment in which at least one of the force resistive objects moves along human tissue under variable forces.

Turning now to FIG. 6, in a particular illustrative embodiment, force resistive objects 102 possess an inner portion 602 made of an inner material and outer portion 604 made of an outer material. In a particular embodiment, the inner portion is a liquid and the outer portion is a flexible material. Turning now to FIG. 7, in a particular illustrative embodiment, the connective members 122 and 124 are made of elastic which can be stretched to allow the force resistive objects to move to different positions 107A and 107B on human tissue by being pulled by the elastic retraction of the connective member under varying forces 710 from the human tissue, as shown in FIG. 7. The varying forces 710 can be varied by adjusting a weight which a human applies while sitting on the force resistive members. In another particular embodiment the connective members are made of elastomeric materials which are stimulated to cause the connective member to expand or contract and move pressure resistive balls connected to the connective members.

Figure 8:
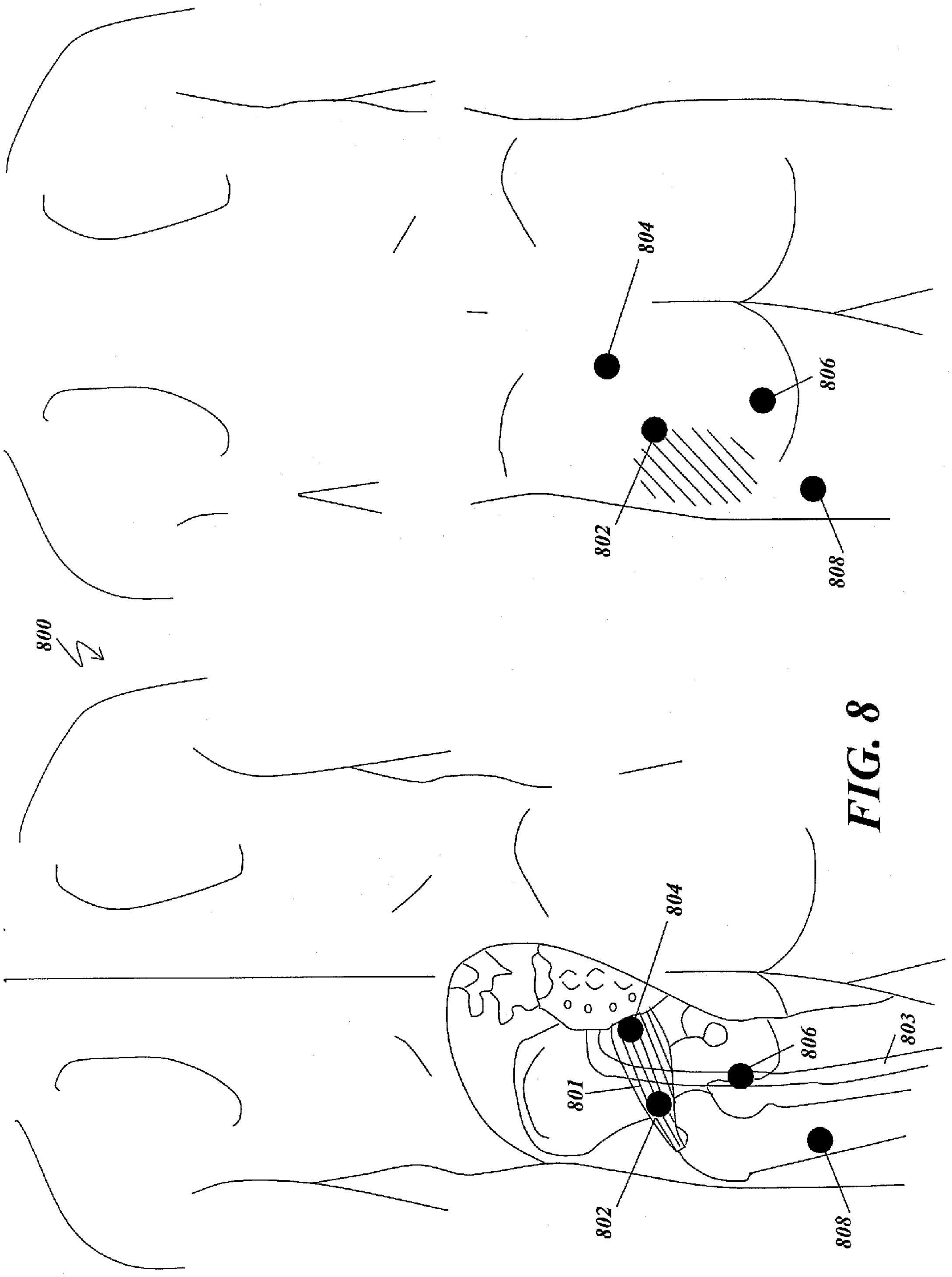
FIG. 8 illustrates human tissue including but not limited to piriformis muscle trigger points and a sciatic nerve for positioning force resistive objects in an illustrative.

Turning now to FIG. 8, a depiction of a portion of the human body 800, including but not limited to bone and skeletal muscle including but not limited to the piriformis muscle 801, having piriformis trigger points 802 and 804, sciatic nerve 803 having nerve contact point 806 and bone 807 having bone contact point 808 on a human body are illustrated. A human can apply pressure concurrently to one of the piriformis trigger points, two of the piriformis trigger points, one or two of the piriformis trigger points and the sciatic nerve point 806 or bone point 808 any combination of nerves, bone and muscle points concurrently.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived there from, such that structural and logical substitutions and changes may be made without departing from the scope of this disclosure. Figures are merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "illustrative embodiment" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37° C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

Although the illustrative embodiment has been described with reference to several illustrative embodiments, it is understood that the words that have been used are words of description and illustration, rather than words of limitation. Changes may be made within the purview of the appended claims, as presently stated and as amended, without departing from the scope and spirit of the illustrative embodiment in its aspects. Although the illustrative embodiment has been described with reference to particular means, materials and embodiments, the invention is not intended to be limited to the particulars disclosed; rather, the invention extends to all functionally equivalent structures, methods, and uses such as are within the scope of the appended claims.

What is claimed is:

1. An apparatus comprising:

a plurality of force resistive pressure-bearing objects lying upon a force resistive plane, for concurrently applying pressure to a plurality of different positions on at least one of a plurality of human tissues; and a non-pressure bearing connective member for flexibly interconnecting the plurality of force resistive objects, wherein a force perpendicular to the force resistive plane exerted on one of the plurality of force resistive pressure-bearing objects is not transmitted to another one of the plurality of force resistive pressure-bearing objects through the non-pressure bearing connective member;

wherein the connective member is elastomeric;

the apparatus further comprising:

an electronic controller for stimulating the elastomeric connective member to contract and expand the elastomeric connective member to change the position of the force resistive pressure-bearing objects.

2. The apparatus of claim 1, wherein the force resistive objects concurrently apply pressure to the human tissues at the plurality of different positions and are flexibly interconnected in a geometric configuration selected from the group consisting of a triangle, rectangle, square, parallelogram and irregular.

3. The apparatus of claim 1, wherein the force resistive pressure-bearing objects have a shaped selected from the group consisting of a pyramid, sphere, square, cylinder and oval.

4. The apparatus of claim 1, wherein the connective member is adjustable to change a distance between at least two of the interconnected force resistive pressure-bearing objects and at least one of the different positions.

5. The apparatus of claim 1, wherein the plurality of force resistive pressure-bearing objects further comprise a material having a property selected from the group consisting of piezoelectric, elastomeric, electro transmissive, heat absorptive, heat generating and cold generating.

6. The apparatus of claim 1, wherein the force resistive pressure-bearing objects further comprise an inner portion comprising an inner material surrounded by an outer portion comprising a flexible material, wherein the inner material is selected from the group consisting of a gel, a liquid, a powder and a solid.

7. The apparatus of claim 1, wherein the connective member is elastic so that when a variable force is reduced on the object and the reduced force allows the elastic connective member when stretched to contract and change position to move the object to different positions on the human tissues.

8. The apparatus of claim 1, wherein the human tissues further comprises tissue selected from the group consisting of bone, muscle and nerve, wherein each of the plurality force resistive pressure-bearing objects resists force from at least one of the human tissues.

9. The apparatus of claim 8, wherein at least two of the force resistive pressure-bearing objects resist force from at least two different positions on at least one of the human tissues.

10. The apparatus of claim 9, wherein at least three of the force resistive pressure-bearing objects resist force from at least two different tissues at separate positions on the human body.

* * * * *